United States Patent [19]

Northemann et al.

[11] 4,131,967
[45] Jan. 2, 1979

[54] TOOTHBRUSH

[76] Inventors: Karl-Heinz Nörthemann, Ringstrasse 18, 3501 Schauenburg 4; Heinrich Krahn, In den Steinäckern 5, 3507 Baunatal 5, both of Fed. Rep. of Germany

[21] Appl. No.: 684,184

[22] Filed: Jul. 1, 1976

[30] Foreign Application Priority Data

Feb. 3, 1976 [DE] Fed. Rep. of Germany ....... 2608532

[51] Int. Cl.² .............................................. A46B 9/04
[52] U.S. Cl. ................................................ 15/167 A
[58] Field of Search ............... 15/167 A, 167 R, 167 B

[56] References Cited

U.S. PATENT DOCUMENTS

| 569,870 | 10/1896 | Hamilton | 15/167 A |
| 1,353,780 | 9/1920 | Mueller | 15/167 A |
| 1,389,624 | 9/1921 | Carroll | 15/167 A |
| 2,077,392 | 4/1937 | Boyd | 15/167 A |

FOREIGN PATENT DOCUMENTS 332091 10/1958 Switzerland .......................... 15/167 A Primary Examiner—Robert W. Jenkins

[57] ABSTRACT

A toothbrush which comprises an elongated handle including a U-shaped head coaxial with a front end of the handle. The head is provided with two opposite bristles-carrying portions located to opposite sides of an axis of the head and each of the portions has a front edge which is inclined at an acute angle to the axis. The toothbrush further includes a plurality of bristle tufts which are spaced from each other inwardly from the bristle-carrying portions and are arranged in a first plurality of rows which is substantially parallel to the front edge and in a second plurality of rows parallel to the axis. The ends of the bristles in the second plurality of rows on the opposite bristles-carrying portions are arranged to define an acute gap therebetween.

2 Claims, 20 Drawing Figures

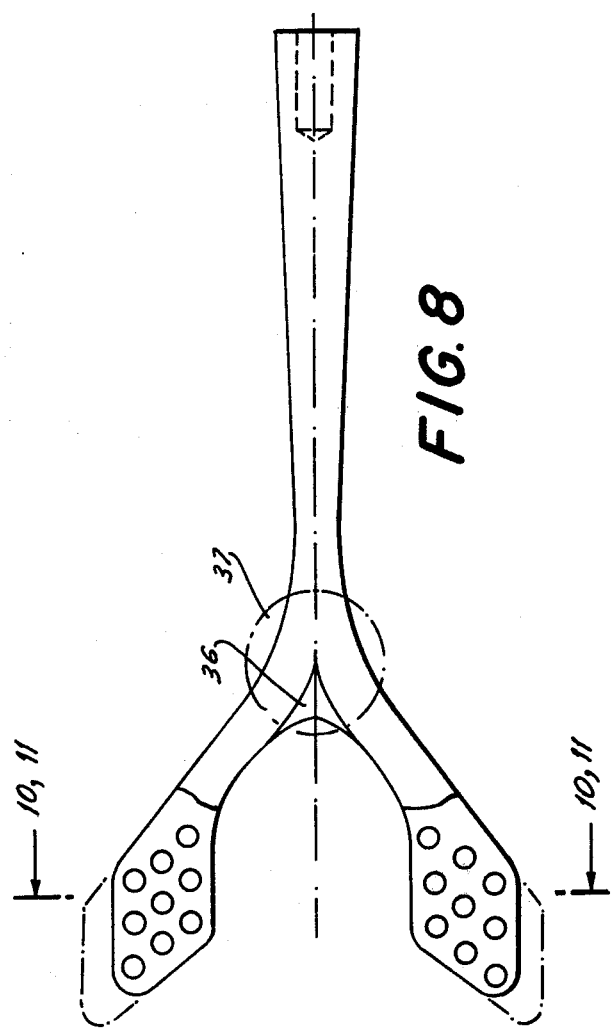
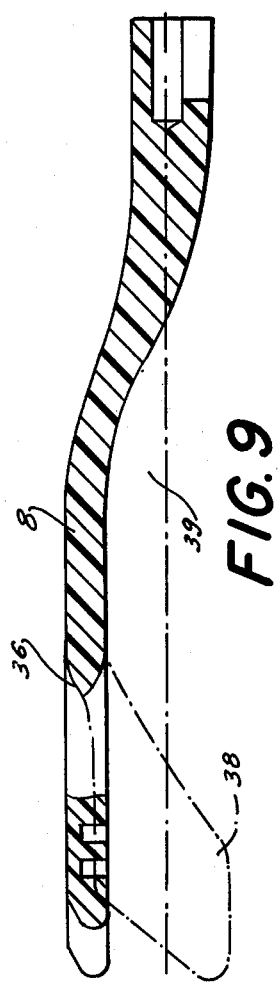
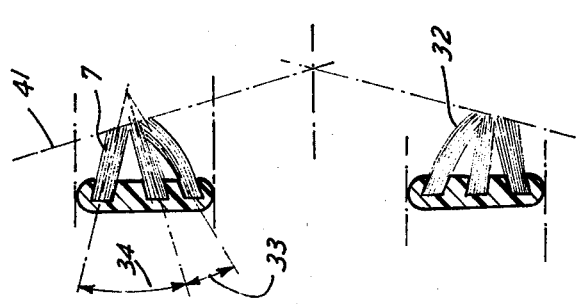
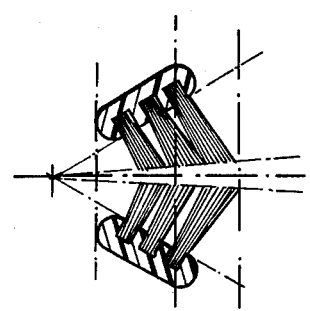
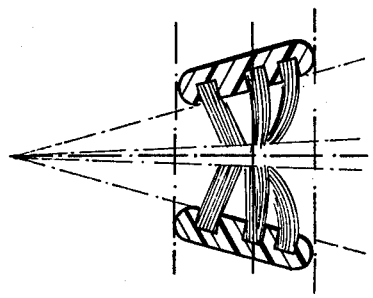

TOOTHBRUSH

BACKGROUND OF THE INVENTION

This invention relates to toothbrushes. More particularly this invention concerns a toothbrush having two-brush heads.

Two-brush head toothbrushes are already well known and normally include a handle which is provided with two bristle-sides which are arranged at a front end of the handle. The two bristle sides are arranged opposite to each other, thereby defining a V-shape form so that bristle-bundles provided at the bristle sides form an intermediate cleft.

It has been recognized that these toothbrushes are not satisfactory with respect to convenience, comfort and efficiency of cleansing of the inner or outer side of the teeth as well as the cleansing of the crowns together with tooth cavities and gingival margins. During the course of brushing the teeth it is very important to properly brush the tooth-cavities and spaces between the teeth, which are sometimes very narrow and almost inaccessible. Under these circumstances a toothbrush must have a possibility to be reciprocated along the teeth as well as moved up and down, to obtain the most desirable brushing effect and to remove tartar and food remnants from the spaces between the teeth, as well as from necks and cavities of the teeth.

SUMMARY OF THE INVENTION

It is a general object of this invention to overcome the above-described disadvantages.

More particularly, it is an object of the invention to provide an improved toothbrush for convenient, comfortable and efficient cleansing of all surfaces of the teeth, together with tooth cavities and gingival margins.

A further object of the present invention is to provide a toothbrush which enables a user to reach all the teeth without discomfort and which permits the reciprocating movement of such a toothbrush along the teeth as well as up and down, in order to get efficient brushing of all surfaces of the teeth.

Pursuant to these objects, and others which will become apparent hereinafter, one feature of the present invention resides in a tooth brush which comprises an elongated handle which has a longitudinal axis, a front end and a rear end, a U-shaped head which is coaxial with the front end of the handle. The head has two opposite bristles-carrying portions located to opposite sides of the axis and each of the bristles-carrying portions has a front-edge inclined at an acute angle to the axis. The bristles-carrying portions are provided with a plurality of bristle tufts which are spaced from each other and project inwardly from the bristle-carrying portions. The tufts are arranged in a first plurality of rows substantially parallel to the front edge and in a second plurality of rows parallel to the axis. The first and second plurality of rows intersect each other at four corner points and the axes of the tufts of bristles at the four corner points which extend with inclination toward each other. The ends of the bristles in the second plurality of rows on the opposite bristle-carrying portions are arranged so as to define an acute gap therebetween. In accordance with another feature of the present invention the handle has rearwardly of the head a portion curved transversely to the axis, so that the end of the handle and the middle of the head are lying on one and the same axis.

Another advantageous feature of the present invention resides in providing the front end of the head of the handle with a slope rearwardly towards the rear end of the handle. This feature renders it possible to reach the rear molars without difficulty and discomfort.

According to another advantageous feature of the present invention a toothbrush is provided with coupling means at the rear end of the handle for coupling means therefor for oscillating the toothbrush about the axis. In other words, the head receives an oscillating movement from the means connected to the rear end of the handle, which means can be mechanical or electrical one. This movement is transmitted to the brush-elements of the head. Besides this an additional movement of the brush relative to its longitudinal axis is possible, as well as up and down, that is an oscillating movement of the toothbrush along the rows of the teeth, thereby obtaining an efficient but still comfortable cleansing of all surfaces of the teeth together with tooth cavities and gingival margins.

BRIEF DESCRIPTION OF THE DRAWINGS

FIG. 8, FIG. 9, FIG. 10, FIG. 11, FIG. 12, FIG. 13 show steps of a method of making the toothbrush in accordance with the present invention.

DESCRIPTION OF THE PREFERRED EMBODIMENT

Figure 15:
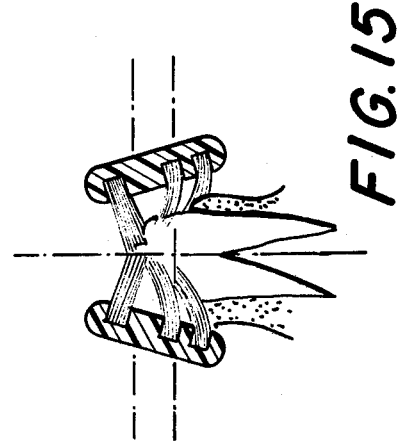
FIGS. 7a through FIG. 7f, FIG. 14, FIG. 15 show usage of the toothbrush.
Figure 1:
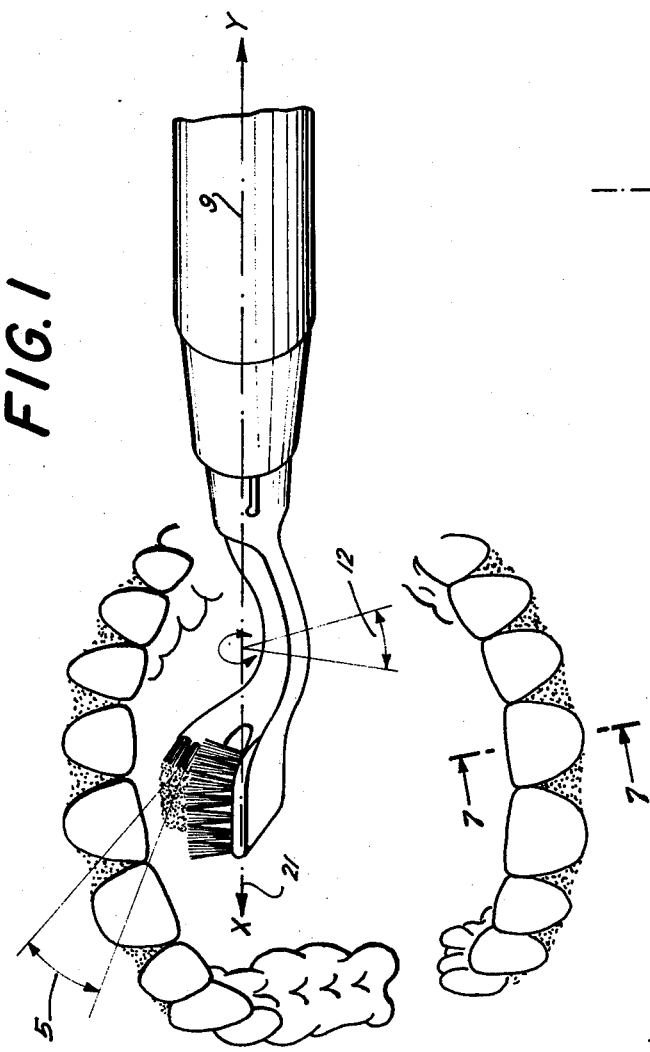
FIG. 1 is a perspective view of a toothbrush in accordance with the present invention.
Figure 14:
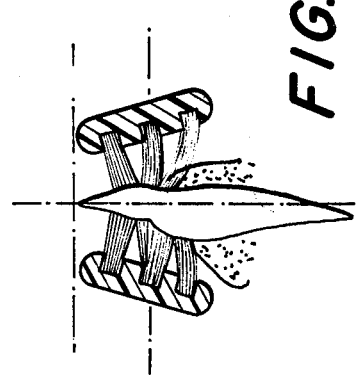
Figure 2:
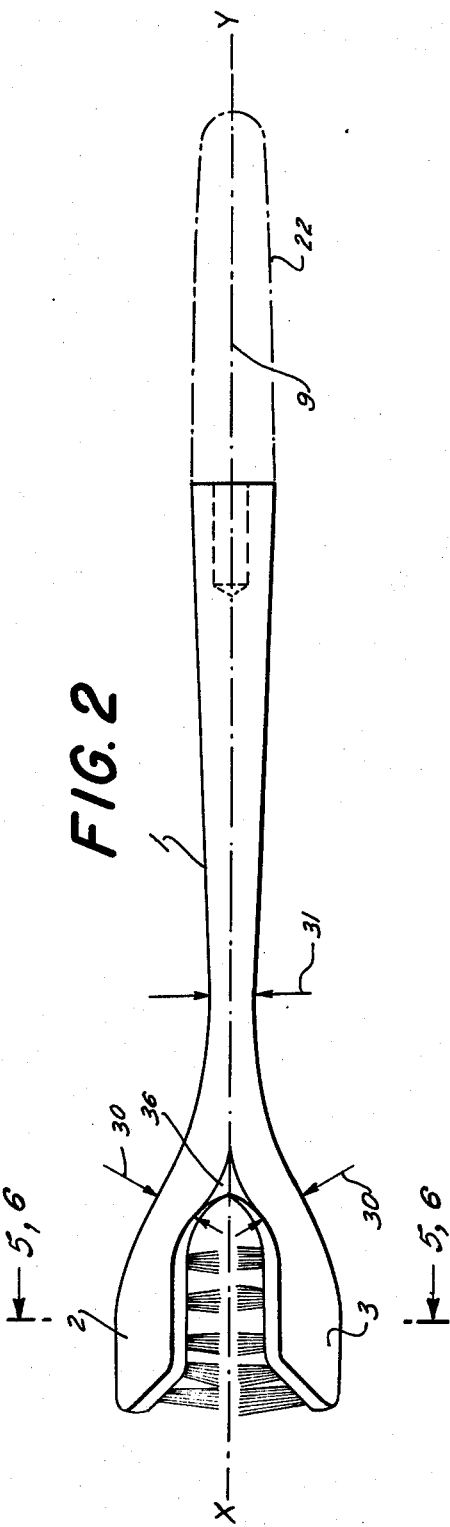
FIG. 2 is a longitudinal view of the toothbrush viewed from the back.

Referring now to the drawings and first to FIG. 2 thereof, it may be seen that the reference numeral 1 is used to designate a handle which has a rear end and a front end. The front end of the handle is provided with a U-shaped head which has two opposite arms 2 and 3. The arms are provided to carry bristle bundles 7, so that the bundles of different arms define a gap 5 (see FIG. 1) therebetween.

Figure 3:
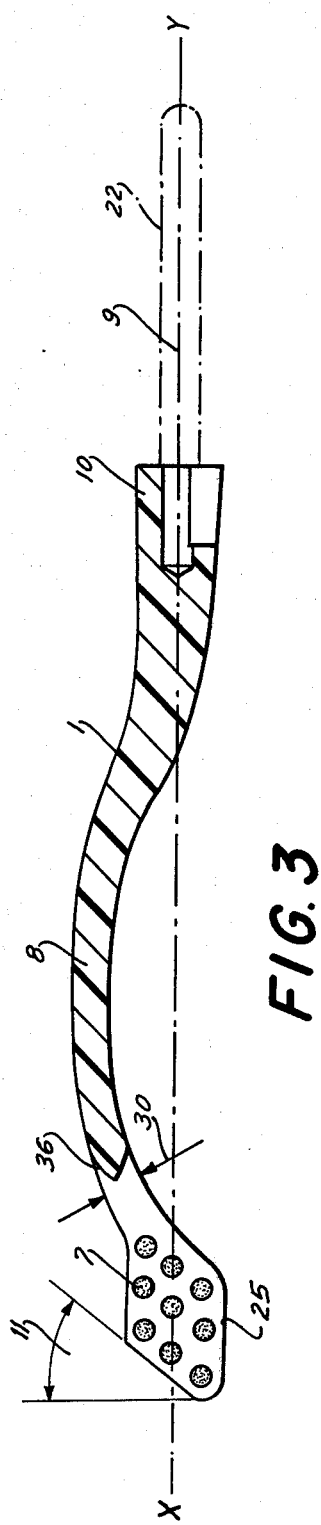
FIG. 3 is a longitudinal sectional view of the toothbrush.

In contrast, to the prior art toothbrushes, which have a handle which is bent only upwardly at its rear portion, the handle 1 of the present invention is bent in such a portion 8 between the end 10 of the handle 1 and the U-shaped head carrying the bristle-bundles, that that end 10 and the head (2, 3) are coaxial, that is they have one and the same axis X-Y (see FIG. 3) of symmetry.

The front ends of both arms 2 and 3 are provided with a slope 11 inclined rearwardly relative to the longitudinal axis 9 of the handle to thereby make it possible to reach the area of the rear molars. Transition zones 30 and a different thickness 31 of the handle along its length are provided to insure convenience, comfort and efficiency of the toothbrush in its usage.

The rear end of the handle 1 is provided with coupling means for connecting to a suitable driving arrangement for subjecting the toothbrush to oscillating movement around the axis 9.

The coupling means can be, for example, accomplished as a socket-switch connection 10, or hand-grip 22. The driving arrangement can be any conventional device, either mechanical or electrical.

Figure 4:
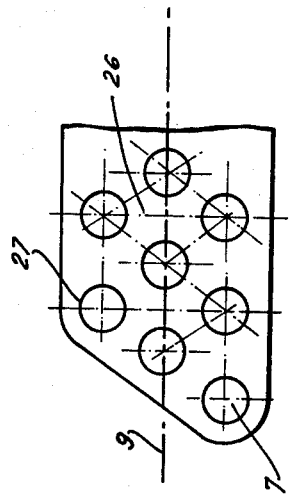
FIG. 4 is a front view of a bristle-carrying portion.

The bristle bundles 7 project inwardly from bristle-carrying arms 2 and 3 and they are spaced from each other so that they bound a first plurality of rows parallel to the front edge of the head and a second plurality of rows parallel to the longitudinal axis 9 (see FIG. 1). The first and second plurality of rows intersect each other at four corner points and are inclined towards each other, thereby defining — if viewed transversely as shown in FIG. 4 — a rhomboid form. Such an arrangement of tufts has the advantage, that it facilitates brushing of the spaces between teeth, which sometimes are very narrow. The ends of bristles in the second plurality of rows on the opposite bristle-carrying arms 2 and 3 are arranged so as to define an acute gap 5 therebetween.

Figure 6:
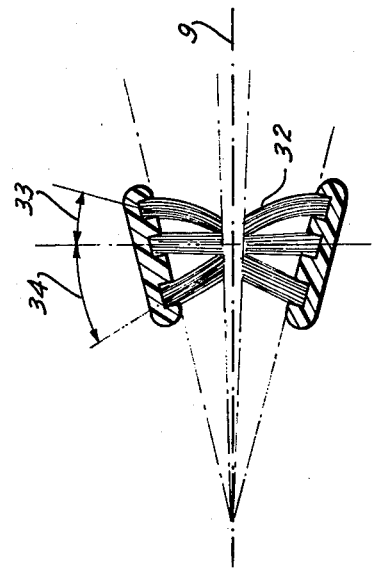
FIG. 6 is a view of bristles, arranged advantageously for cleansing and massaging the gingival.
Figure 5:
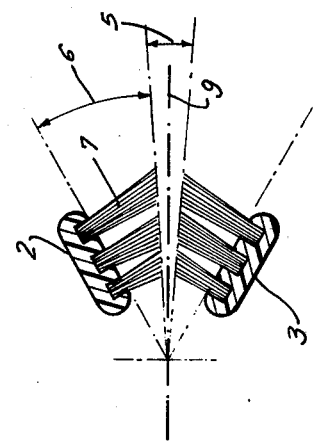
FIG. 5 is a view of bristles, arranged for cleaning the teeth.

The ends of the bristles are drawn back vertically and/or transversely to the longitudinal axis 9 (see FIGS. 10 and 11) to define a first imaginary edge 40 positive relative to the axis 9 as well as a second imaginary edge 41 which is negative relative to the axis 9. When the bristles 7 are folded on the arms 2 and 3 they define different bristle positions (see FIGS. 6 and 13) relative to the axis 9. The position shown on FIGS. 5 and 12 is advantageous for cleansing all surfaces of the teeth, whereas the position shown in FIGS. 6 and 13 is particularly advantageous for cleansing and massaging of the gingival. The bristles which are arranged in interim bristle rows with a negative inclination relative to the axis 9, are operative when the gingival is being brushed. This row performs a care effect for the gingival, whereas the upper rows perform cleansing and massaging effects.

Important cleansing in the spaced between the teeth and in the gingival spaces as well as tooth cavities will be obtained by penetrating of the bristles into said cavities and spaced when applying to the toothbrush an additional oscillation about the axis 9.

Figure 7A:
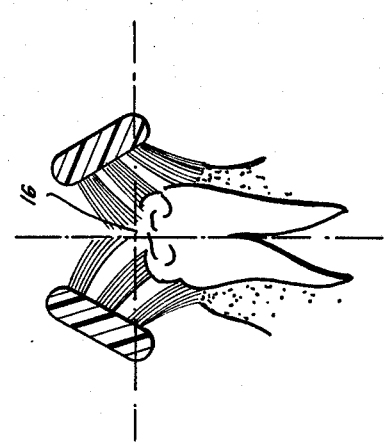
Figure 7B:
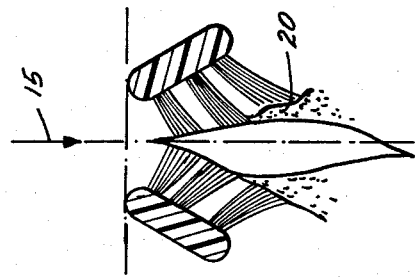
Figure 7C:
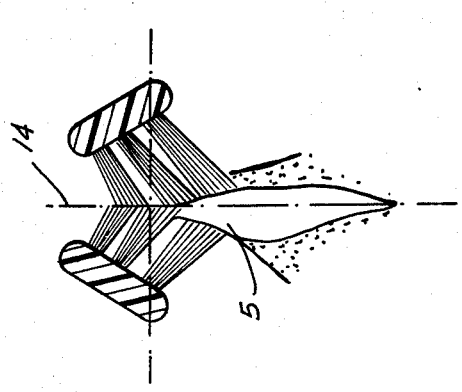
Figure 7D:
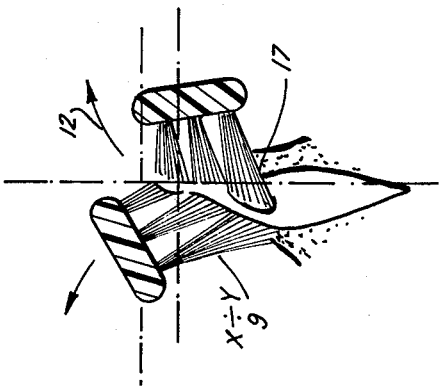
Figure 7E:
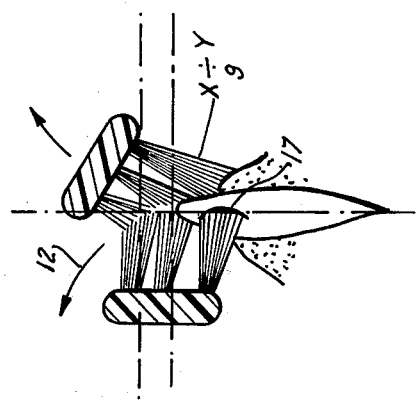
Figure 7F:
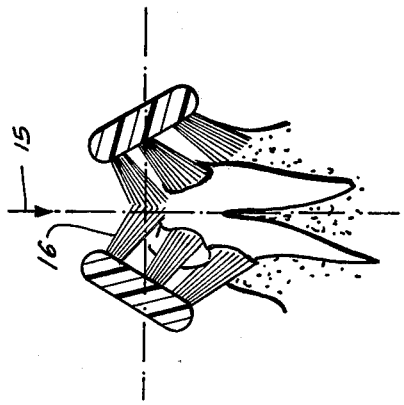

During operation, for example during brushing of the incisors 14 (see FIG. 7a), the brush executes an angular movement 12 back and forth along the axis 9. Meanwhile the bristles 7 are oscillated in order to pass through into tooth-cavities, tooth-spaces and fissures 17 from the front and the back side of the teeth, and also to massage the gingival 20. As a result of these motions the brush removes all film and food particles and stimulates circulation. The oscillating brush can be just pushed along the teeth and the brush will be automatically guided by the curve of the row of teeth. An excellent cleansing as well as massage of the gingival will be accomplished mechanically as shown on FIGS. 7a through 7f, at 14 and 15, by applying light pressure to the handle.

A method of making a toothbrush according to the present invention is as follows:(see FIGS. 8, 9, 10, 11, 12, 13).

A workpiece of synthetic plastic material is shaped for example injection molded, in order to obtain a flat-shaped handle provided with a fork-shaped head. The portion of the handle from the middle of the latter up to the front end thereof is then offset relative to the longitudinal axis of the handle, so as to form a curve 39.

The partly finished curve portion 8 is then subjected to the final shaping, for example, by thermoplastic treatment 37, so as to fold and shape towards each other (38) the two arms 2 and 3 of the fork-shaped head. The head as folded has a common axis X-Y(a). The folding can be accomplished in a forming die. The portion 36 which has the form of a blunt point, renders it possible to perform deformation of the fork-shaped head without creating any creases in the material of the same.

The installing of the bristle bunches is effected with a flat axis either normally or at any different angles to the head and the bristles are then trimmed at any desired inclination relative to the axis of the handle. These steps are carried out before thermoplastic shaping.

We claim:

1. A toothbrush comprising an elongated handle having a longitudinal axis, a front end and a rear end, a U-shaped head coaxial with said front end of the handle, said head having two opposite bristles-carrying portions located to opposite sides of said axis and each of said bristles-carrying portions having a front edge inclined at an acute angle to said axis; and a plurality of bristle tufts projecting spaced from each other inwardly from said bristles-carrying portions and being arranged in a first plurality of rows substantially parallel to said front edge and in a second plurality of rows parallel to said axis, said first and second plurality of rows intersecting each other at four corner points and the axes of the tufts of bristles at said four corner points extending inclined toward each other and the ends of said bristles in said second plurality of rows on said opposite bristles-carrying portions being arranged to define an acute gap therebetween, said handle having rearwardly of said head a portion curved transversely to said axis.

2. A toothbrush as defined in claim 1 and including coupling means at said rear end of said handle for coupling means thereto for oscillating said toothbrush about said axis.

* * * * *